(12) United States Patent
Wiederin

(10) Patent No.: US 8,118,050 B1
(45) Date of Patent: Feb. 21, 2012

(54) ON-LINE CONSTANT FLOW DILUTION

(75) Inventor: Daniel R. Wiederin, Omaha, NE (US)

(73) Assignee: Elemental Scientific Inc., Omaha, NE (US)

( * ) Notice: Subject to any disclaimer, the term of this patent is extended or adjusted under 35 U.S.C. 154(b) by 635 days.

(21) Appl. No.: 11/701,668

(22) Filed: Feb. 2, 2007

(51) Int. Cl.
- *G05D 11/13* (2006.01)
- *F17D 1/14* (2006.01)
- *F01B 25/02* (2006.01)
- *G01N 1/38* (2006.01)

(52) U.S. Cl. ............... 137/93; 137/111; 137/565.33; 137/625.46

(58) Field of Classification Search ............ 137/2, 3, 137/88, 89, 93, 101.19, 111, 109, 597, 599.01, 137/599.03, 599.06, 599.12, 625.46, 595; 73/863.31, 863.41
See application file for complete search history.

(56) References Cited

U.S. PATENT DOCUMENTS

| | | | | | |
|---|---|---|---|---|---|
| 2,105,198 | A | * | 1/1938 | McNamara | 137/555 |
| 4,108,602 | A | * | 8/1978 | Hanson et al. | 436/52 |
| 4,520,108 | A | * | 5/1985 | Yoshida et al. | 436/52 |
| 5,077,017 | A | * | 12/1991 | Gorin et al. | 422/514 |
| 5,308,583 | A | * | 5/1994 | Sanuki | 422/100 |
| 5,826,749 | A | * | 10/1998 | Howland et al. | 222/1 |
| 6,998,095 | B2 | * | 2/2006 | Anderson et al. | 422/103 |
| 7,306,765 | B2 | * | 12/2007 | Davis et al. | 422/62 |
| 2003/0224532 | A1 | * | 12/2003 | Smith et al. | 436/180 |
| 2006/0104827 | A1 | * | 5/2006 | Shaw et al. | 417/245 |

* cited by examiner

*Primary Examiner* — John Rivell
*Assistant Examiner* — Atif Chaudry
(74) *Attorney, Agent, or Firm* — Advent IP, P.C., L.L.O.

(57) ABSTRACT

A system for providing constant flow on-line dilution comprising a first fluid introduction line carrying a first fluid, a second fluid introduction line carrying a second fluid, a flow path selection assembly coupled to the fluid introduction line and the second fluid introduction line, a mixing assembly suitable for mixing the first fluid, the second fluid and a sample, and a plurality of fluid transport lines coupled to the flow path selection assembly suitable for transporting the first fluid, the second fluid and a sample to the mixing assembly. The flow path selection assembly is suitable for selecting a flow path for each of the first fluid introduction line and second fluid introduction lines and providing changeable coupling of each of the first fluid introduction line and second fluid introduction line to one of the plurality of fluid transport lines through the flow path selection assembly.

20 Claims, 4 Drawing Sheets

ON-LINE CONSTANT FLOW DILUTION

FIELD OF THE INVENTION

The present invention relates generally to laboratory equipment, and more particularly to a system and apparatus of providing on-line constant flow sample dilution.

BACKGROUND OF THE INVENTION

Dilution is utilized in analytical laboratories for various purposes, including preparation of calibration standards, to bring sample concentrations within instrumental working ranges, and to reduce matrix effects. In a sample introduction system, it is often necessary to dilute a solution prior to analysis by an analyzer such as an Inductively Coupled Plasma Mass Spectrometer (ICP-MS). Dilution may be necessary for a sample that is out of range of the analyzer, such as a high concentration analyte, or to correct a quality control error. Dilution may be accomplished off-line, in a sample preparation area, or online at the ICP-MS. On-line dilution may be advantageous as it minimizes the steps required for preparation of a sample for analysis. Disadvantageously, the need to dilute a solution prior to analysis may be a time-consuming operation. As a result, several techniques providing automated on-line sample dilution have been developed. However, dilution with all of these techniques is generally accomplished by varying the pump speeds of the pumps to increase or decrease the ratio of the flow rates of the introduced sample and the diluent to be mixed with the sample. For example, the relative speed of two or more pumps each carrying a solution may be increased and decreased with respect to one another depending on a selected dilution factor. This constant variation of pump speed of two or more lines carrying a diluent and a sample creates inefficiency in sample analysis as it requires constant monitoring and calibration of pump equipment, flow rates and diluent ratios. Furthermore, many of these techniques require a vacant line to transfer a diluted sample to an analyzer.

Consequently, it is desirable to provide on-line constant flow sample dilution that does not require a change in pump speed to vary sample to diluent ratio when diluting a sample for analysis.

SUMMARY OF THE INVENTION

Accordingly, the various embodiments of the present invention are directed to a system and method of providing constant flow on-line dilution for a sample in a laboratory environment.

In accordance with a first aspect of the present invention, a system for providing constant flow on-line dilution is disclosed. System may be suitable for introducing a diluted sample to an ion source of a mass spectrometer. System may comprise a first fluid introduction line, a second fluid introduction line, a flow path selection assembly, a plurality of fluid transport lines, a mixing assembly and a transport line suitable for transporting a mixed solution to an analyzer. First and second fluid introduction lines may each comprise a fluid introduction device suitable for introducing a fluid into the fluid introduction line and a pump assembly suitable for pumping a fluid from a first end of the fluid introduction line through the flow path selection assembly and the mixing assembly to a transport line. Flow path selection assembly may comprise a valve assembly suitable for switching the flow paths of the first and second fluid introduction lines prior to introduction of a sample to the system. Flow path selection assembly may comprise a controller electronically coupled to the valve assembly suitable for determining a flow path for each of the first and second fluid introduction lines and transmitting a determined flow path to the valve assembly. System may further comprise a sample injection assembly suitable for injecting a sample into the system. Sample injection may occur after the flow path selection assembly has selected a path for each of a first fluid and a second fluid introduced into the system.

In accordance with a second aspect of the present invention, a method for providing constant flow on-line dilution is disclosed. Method may comprise providing a first fluid introduction line carrying a first fluid at a first flow rate. Method may also comprise providing a second fluid introduction line carrying a second fluid at a second flow rate. Method may select a path through the flow path selection assembly for each of the first and second fluid introduction lines. Method may transfer the first and second fluids to first and second fluid transport lines. Selection of a first or a second fluid transport line for the first and second fluids may depend on the flow path selected by the flow path selection assembly. Method may also comprise introducing the sample to one of the first or second fluid transport lines. Method may then mix the contents of the first and second transport lines in a mixing assembly and transfer the mixed solution to an analyzer.

It is to be understood that both the foregoing general description and the following detailed description are exemplary and explanatory only and are not restrictive of the invention claimed. The accompanying drawings, which are incorporated in and constitute a part of the specification, illustrate an embodiment of the invention and together with the general description, serve to explain the principles of the invention.

BRIEF DESCRIPTION OF THE DRAWINGS

The numerous objects and advantages of the present invention may be better understood by those skilled in the art by reference to the accompanying figures in which.

DETAILED DESCRIPTION OF INVENTION

Figure 1A:
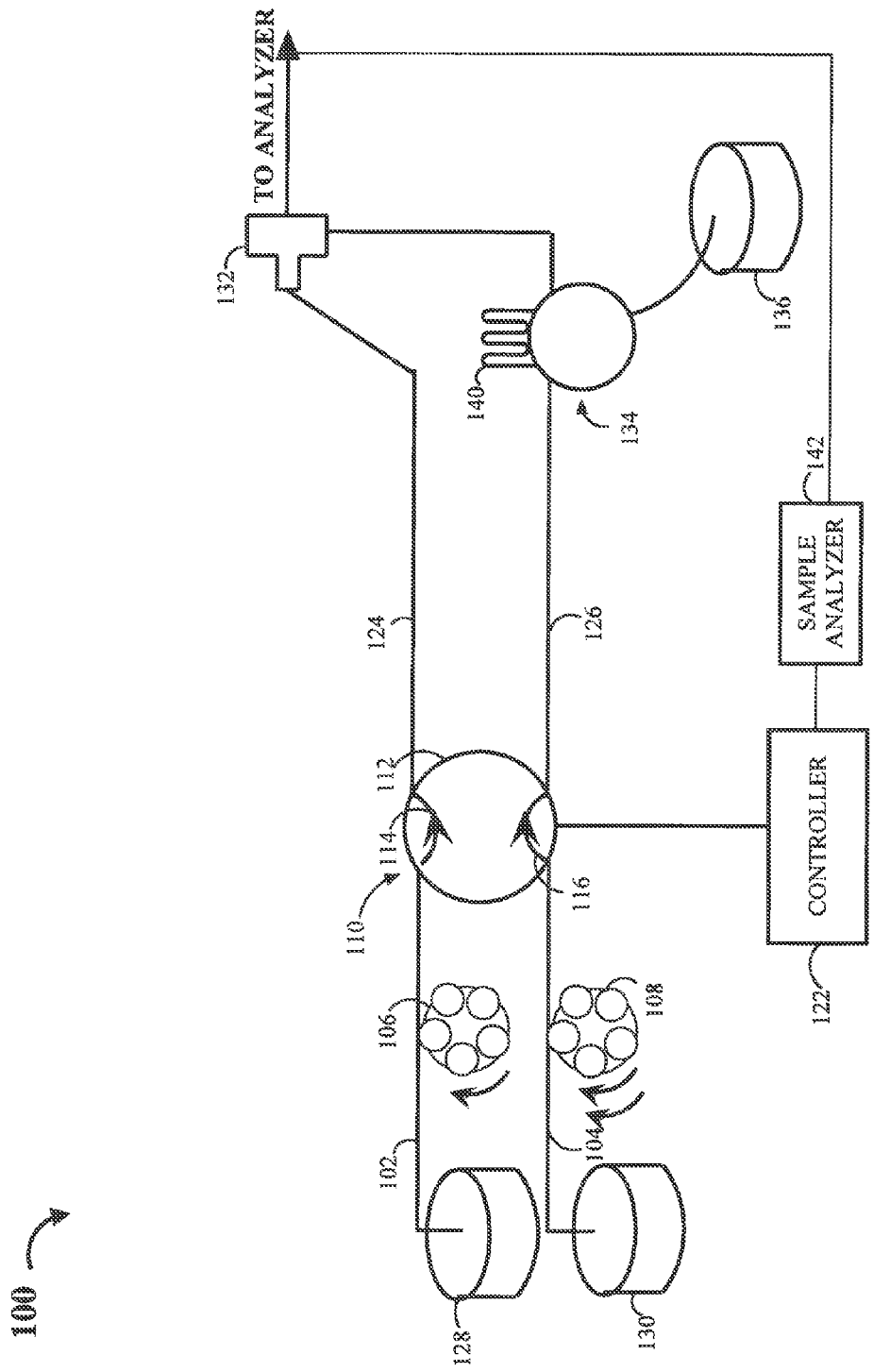
FIGS. 1A and 1B are schematic diagrams illustrating a system in accordance with an exemplary embodiment of the present invention.

Reference will now be made in detail to the presently preferred embodiments of the invention, examples of which are illustrated in the accompanying drawings.

Referring to FIG. 1, a block diagram illustrating a system 100 in accordance with an exemplary embodiment of the present invention is shown. System 100 may comprise a plurality of fluid introduction lines. For example, system 100 may comprise a first fluid introduction line 102, and a second fluid introduction line 104. The tubing or pipe components of the fluid introduction lines may be composed of suitably rigid materials to prevent expansion or contraction under any pressure. Such expansion or contraction is undesirable as it may affect the volume occupied by the sample, diluent and diluted sample. However, expansion and contraction may be tolerated if the extent is determinable or predictable.

First fluid introduction line 102 and second fluid introduction line 104 may be respectively coupled to first and second mechanical devices 106, 108 suitable for providing movement of a fluid within the first fluid introduction line 102 and the second fluid introduction line 106 from a first point to a second point in the system. Mechanical devices 106, 108 may be a pumping device such as a motorized or non-motorized pumping device. Fluid may refer to any subset of the phases of matter, including, but not limited to, liquids, gases, plasmas, plastic solids and the like.

A diluent may be introduced into the system via each of the first or second fluid introduction lines 102, 104 by respective first and second pumping devices 106, 108. In one embodiment, first and second pumping devices 106, 108 may each be a peristaltic pump. A peristaltic pump may be a pump utilizing rotating rollers pressed against special flexible tubing to create a pressurized flow. The tube is compressed at a number of points in contact with the rollers or shoes. The media is moved through the tube with each rotating motion. The individual components of a peristaltic pump may be comprised of a pump head, drive, and tubing. A peristaltic pump may also be referred to as a flexible member pump, a flexible tube pump, a dispensing pump, or a dosing pump. It is further contemplated that pump may be a syringe pump suitable for pumping an amount of fluid at a desired flow rate. It is further contemplated that pumping device 106, 108 may be a piston type pump, or any other such pumping device suitable for continuous pumping of relatively large or small volumes of fluid.

The first and second pumping devices 106, 108 may be individually controlled by flow rate controllers. Flow rate information or data may be transmitted from the pumps, or flow meters back to the flow rate controllers, and a flow rate for each pump may be determined. The first and second pumping devices provide a substantially continuous flow, without pulsing or other such flow interruptions. The flow rate from each pump may be determinable via be independent flow meters disposed before or after of each pump, respective of the flow direction with an appropriate feedback loop to the pump controller. Alternatively, the dilution factor may be measurable by the use of an internal standard. An appropriate software program may be utilized by the pump controllers to automate the dilution of the samples and change-over from one sample to the next. In one embodiment, pump controllers may comprise a desktop PC with appropriate input and output devices to monitor and control the pumps via the software program.

It is further contemplated that both the first fluid introduction line 102 and the second introduction line 104 may be coupled to one pumping device. The pumping device may be suitable for providing a first flow rate for a first introduction line and a second flow rate for a second fluid introduction line.

A fluid may be introduced into the system 100 at substantially one end of each of the first and second fluid introduction lines. System 100 may comprise a first fluid introduction device 128 coupled to a first end of the first fluid introduction line and a second fluid introduction device 130 coupled to a first end of the second fluid introduction line. Fluid may be a diluent, an internal standard, a spike, or any other fluid suitable for mixing with a sample prepared for analysis. A diluent may be defined as any liquid or solid material used to dilute or carry an active ingredient. An internal standard may refer to a compound added to each analysis that is used in analyte quantitation. An internal standard may be utilized to verify instrument response and retention time stability. Additionally, an internal standard may be added to a sample extract just before instrumental analysis to permit correction for inefficiencies. A spike may refer to a form of a chemical element having one or more isotope abundance artificially enhanced compared with the natural element. In the preferred embodiment, fluid may be a diluent and may be drawn from a diluent container into at least one or both of the first and second fluid introduction lines.

Figure 2:
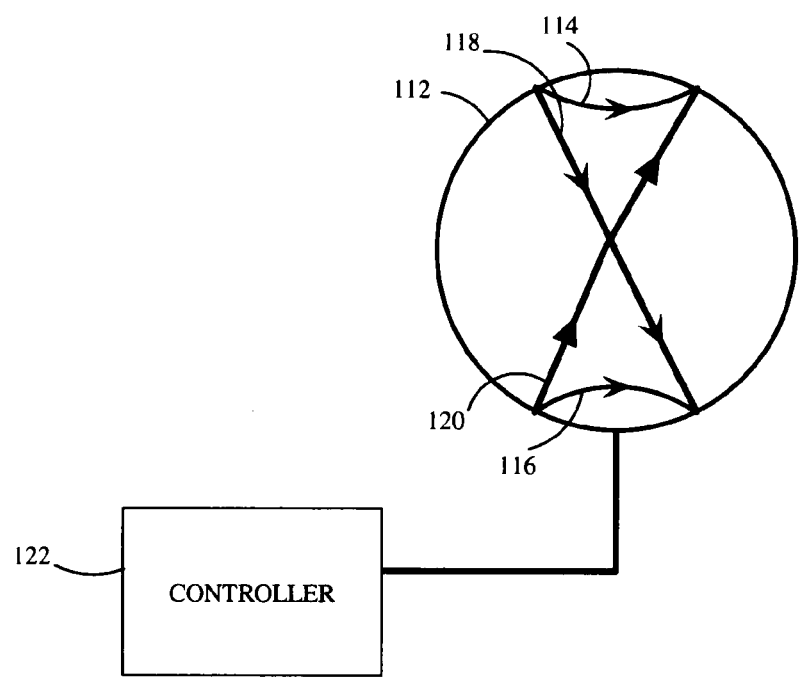
FIG. 2 is an illustration of a flow path selection assembly of a system in accordance with an exemplary embodiment of the present invention.

System 100 may also comprise a flow path selection assembly 110 suitable for selecting a flow path for each of the plurality of fluid introduction lines. Referring to FIG. 2, a top view of a flow path selection assembly 110 in accordance with an exemplary embodiment of the present invention is shown. Flow path selection assembly 110 may comprise a housing 112, a plurality of flow path connector assemblies 114-120 disposed substantially inside the housing, and a controller 122 electronically coupled to the housing 112 suitable for controlling flow path selection through the flow path selection assembly 110. Data from instrument analysis may be input into the controller 122. Controller 122 may utilize this data to determine an appropriate flow path for each of the first and second fluid introduction lines 102, 104. Providing a feedback of data from the analyzer 142 to the flow path selection assembly controller 122 may provide near instantaneous automatic control of the amount by which the sample is diluted. This reduces the need for operator intervention, for instance, and may greatly improve the time efficiency of the analyzer 142. First and second fluids may be substantially similar, or may be different as may be required by the system 100. To this end, flow path selection assembly may comprise a plurality of flow path connector assemblies 114-120 suitable for maintaining a constant fluid flow from a first fluid introduction line through the flow path selection assembly to one of a plurality of fluid transport lines suitable for transporting a fluid to the mixing assembly. Likewise, flow path selection assembly 110 may be suitable for providing a constant fluid flow from second fluid introduction line through the flow path selection assembly to another of the plurality of fluid transport lines suitable for transporting a fluid to the mixing assembly. Fluid flow may be at the same rate for both the first and second fluid introduction lines, or may vary as desired by a user.

The ratio of sample to diluent to be transported to an analyzer is determined by the flow path selection assembly. For instance, a first pumping device pumping fluid through a first fluid introduction line 102 may pump a fluid at a rate of x. A second pumping device pumping fluid through a second fluid introduction line may pump a fluid at a rate of $1/x$. It is to be noted, however, that first and second flow rate ratio may be any ratio of values, and may not be limited to inverse proportions as described in this example, which is just one of several flow rate ratios suitable for a system 100 contemplated by the various embodiments of the present invention. Flow path selection assembly 110 may select a first path for the fluid flowing through the first fluid introduction line. The first path may direct the fluid from the first fluid introduction line 102 through a first path connector 114 of the flow path selection assembly 110 to the mixing assembly via a first transport line 124 at flow rate x. Flow path selection assembly 110 may select a second path for the fluid flowing through the second fluid introduction line 104. To accomplish flow path selection through the flow path selection assembly, flow path selection assembly housing may comprise a plurality of apertures suitable for receiving at least one end of the first fluid introduction line, the second fluid introduction line and the plurality of fluid transport lines. The second path may direct the fluid from the second fluid introduction line through a second path connector 116 to a second transport line 126. A sample may be loaded in the system by delivery to one of the first or second fluid transport lines by a first pumping device. Specifically, system 100 may comprise a sample injection assembly 134 suitable for injecting a sample into one of the first fluid transport line or the second fluid transport line. A sample may be introduced into the system at a point after the flow path selection assembly. Sample may be introduced to one of the first or second fluid transport lines along with an internal standard for dilution factor correction. Sample injection assembly 134 may further comprise a valve, a sample injection pump and a sample container 136. A small amount of sample may be utilized to fill an injection loop 140. The contents of the loop 140 may then be transported via the carrier stream to, for example, a mixing assembly, an ICP MS and the like. Advantageously, introducing the sample into the system just prior to mixing prevents the sample from flowing through the pumping system.

Figure 1B:
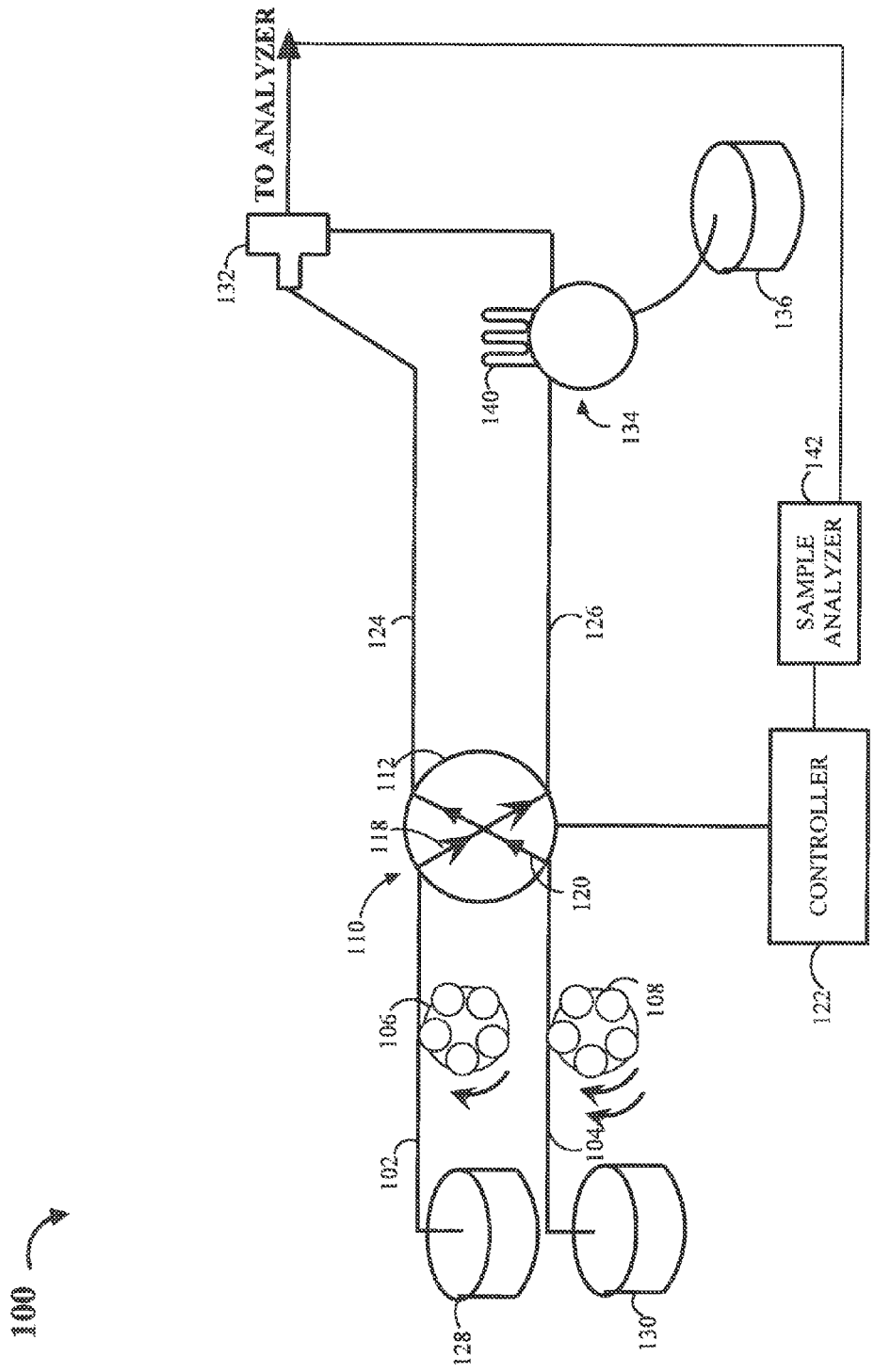

In the embodiment illustrated in FIGS. 1A and 1B, second transport line 126 may be coupled to the sample injection assembly. The fluid flowing through the second transport line 126 may transport a sample introduced to the system 100 via the sample injection assembly 128 through the second transport line 126 to a mixing assembly 132 via the second fluid transport line 126 at flow rate 1/x.

Conversely, flow path selection assembly 110 may select a third path for the fluid flowing through the first fluid introduction line 102. The third path (e.g., the path from the first fluid introduction line 102, through the third path connector 118, and to the second transport line 126) may direct the fluid from the first fluid introduction line 102 through a third path connector 118 of the flow path selection assembly 110 to the mixing assembly 132 via the second transport line 126 at flow rate 1/x. Flow path selection assembly 110 may select a fourth path for the fluid flowing through the second fluid introduction line 104. The fourth path (e.g., the path from the second fluid introduction line 104, through the fourth path connector 120, and to the first transport line 124) may direct the fluid from the second fluid introduction 104 line through a fourth path connector 120 to the first transport line 124. The fluid flowing through the second transport line 126 may transport the sample introduced at the sample injection point through the second transport line 126 to the mixing assembly 132 via the second fluid transport line 126 at flow rate x, and the diluent may be transported to the mixing assembly 132 at a flow rate of 1/x. In this manner, the amount of diluent mixing with the sample may be modified by modifying the path of the first and second fluid introduction lines through the system to the mixing assembly 132. Therefore, the ratio of flow rates may be modified without altering the pump speed for either of the pumps pumping the first and second fluids through the first and second fluid introduction lines.

System 100 may further comprise a mixing assembly 132 suitable for mixing an introduced sample and a diluent. Mixing assembly 132 may be configured from one or more pipes or tubes joined to substantially form a "Y" or "T" shaped configuration. In one embodiment, the mixing assembly 132 is configured as a "mixer-tee" such that it introduces substantial direction change in the flow of the diluent and sample to thereby induce mixing. Specifically, mixing occurs as a function of the turbulent flow of the sample and diluent at and also by diffusion of the two fluids. The mixing assembly is preferably configured to ensure full mixing of the sample and diluent by creating the turbulent flow in the mixing region of the assembly. It is further contemplated that mixing may be completed before the diluted sample enters the analyzer. In this fashion, sufficient equilibration of the mixed sample and diluent is achieved. It is contemplated that a mixing assembly may comprise a plurality of receiving apertures to enable receiving of more than two fluid transport lines. For instance, mixing assembly may be substantially "W" shaped to receive three fluid transport lines, or may comprise more than three apertures to receive more than three fluid transport lines. Other, more complex arrangements of pipe joints may be utilized which ensure thorough mixing of the fluids entering the mixing region from the first and second pipes. The exit of the mixing section comprises a single line disposed between the mixing assembly and a pump suitable for pumping fluid from the mixing assembly to an instrument (not shown) for analysis.

Following the mixing of a sample and a diluent in the mixing assembly 132, any surplus flow may be directed to a drain. An internal standard may be added to a diluted sample via an onboard pump. Following the mixing of the diluted sample and the internal standard, the solution may be provided to an analytical instrument. The analytical instrument may comprise either an ICP mass spectrometer (ICP-MS), an ICP optical analyzer, a flame spectrophotometer, an Atmospheric Pressure Chemical Ionization (APCI) mass spectrometer, or an Electrospray Ionization (ESI) mass spectrometer.

It is further contemplated that a system in accordance with the various embodiments of the invention described may comprise a plurality of fluid introduction lines comprising fluid flowing at a plurality of flow rates, and may not be limited to first and second fluid introduction lines. System 100 may comprise first, second, third, fourth and the like fluid lines and may be suitable for selecting a flow path for each fluid introduction line. Similarly, in a preferred embodiment, system flow path selection assembly may comprise at least enough path connectors to provide a path connection to a fluid transport line for each fluid introduction line contemplated by the system, but may comprise more or less path connectors than fluid introduction lines. Also, system 100 may comprise at least enough transport lines connected to the path connectors to provide transport to the mixing assembly, but may also provide a fewer or greater number of transport lines as may be required or desired.

Examples of samples used by embodiments of the present invention include drinking water, waste water, sea water, diluted acids, urine, blood, spinal fluid, dissolved solid or gaseous samples, or the like. These examples are by no means exclusive, and any liquid sample which requires analysis can be diluted prior to entering the analyzer by pumps which embody the present invention. Of course, an appropriate diluent is required for different samples and the choice of diluent for a given sample does not form part of the present invention. The diluent may be de-ionized water, ethanol or the like, but whatever is most suitable depending on the sample being analyzed.

Figure 3:
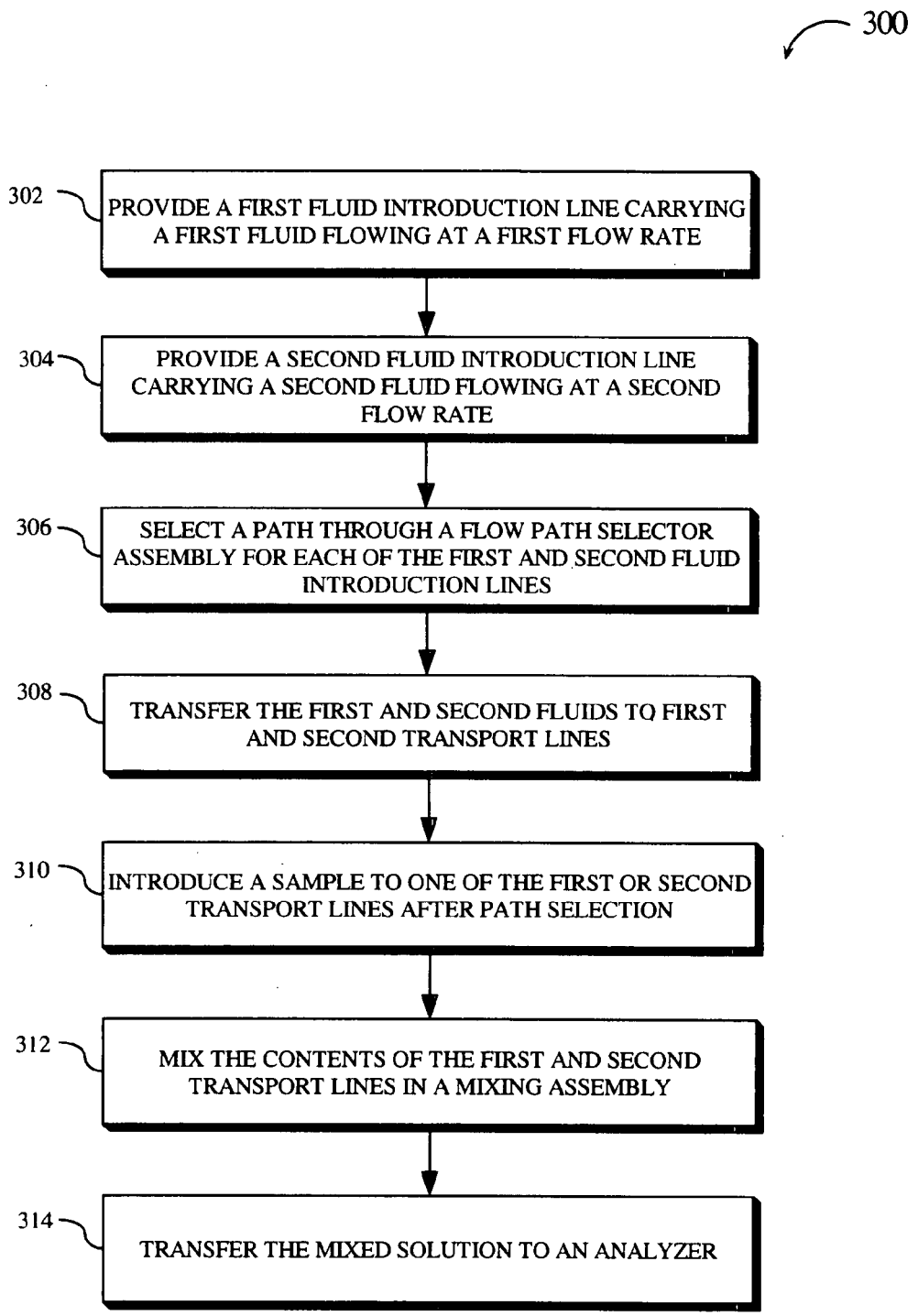
FIG. 3 is a flow diagram illustrating a method in accordance with an exemplary embodiment of the present invention.

Referring to FIG. 3, a flow diagram illustrating a method 300 in accordance with an exemplary embodiment of the present invention is shown. Method 300 may comprise providing a first fluid introduction line carrying a first fluid at a first flow rate 302. Method 300 may also comprise providing a second fluid introduction line carrying a second fluid at a second flow rate 304. First and second fluids may be the same fluid, such as a diluent, internal standard, spike or any combination of these or other fluids suitable for mixing with a sample to be analyzed by an analyzer such as an ICP mass spectrometer. Introduction line may be defined as a fluid carrying line carrying a fluid into the system to a flow path selection assembly 110. Method 300 may select a path through the flow path selection assembly for each of the first and second fluid introduction lines 306. Method may transfer the first and second fluids to first and second transport lines 308. Transport line may be defined as a fluid carrying line carrying the first and second fluids to a mixing assembly. Selection of a first or a second transport line for the first and second fluids may depend on the flow path selected by the flow path selection assembly 110. Method may also comprise introducing the sample to one of the first or second fluid transport lines 310. Sample introduction occurs after flow path selection. Method may then mix the contents of the first and second transport lines in a mixing assembly 312 and transfer the mixed solution to an analyzer 314.

It is understood that the specific order or hierarchy of steps in the foregoing disclosed methods are examples of exemplary approaches. Based upon design preferences, it is understood that the specific order or hierarchy of steps in the method can be rearranged while remaining within the scope of the present invention. The accompanying method claims present elements of the various steps in a sample order, and are not meant to be limited to the specific order or hierarchy presented.

It is believed that the present invention and many of its attendant advantages will be understood by the foregoing description. It is also believed that it will be apparent that various changes may be made in size, materials, shape, form, function, manner of operation, assembly and use of the components thereof without departing from the scope and spirit of the invention or without sacrificing all of its material advantages. The form herein before described being merely an explanatory embodiment thereof. Further, it is contemplated that the specific order or hierarchy of steps in the method can be rearranged while remaining within the scope and spirit of the present invention. It is the intention of the following claims to encompass and include such changes.

What is claimed:

1. A system for providing constant flow on-line dilution comprising:
   a first pumping device configured to pump at a first flow rate;
   a first fluid introduction line for carrying a first fluid, the first fluid introduction line coupled to the first pumping device for pumping the first fluid at the first flow rate;
   a second pumping device configured to pump at a second flow rate at least substantially different from the first flow rate;
   a second fluid introduction line for carrying a second fluid, the second fluid introduction line coupled to the second pumping device for pumping the second fluid at the second flow rate;
   a flow path selection assembly coupled to the first fluid introduction line and the second fluid introduction line;
   a mixing assembly for mixing the first fluid, the second fluid and a sample;
   a plurality of fluid transport lines coupling the flow path selection assembly to the mixing assembly, the plurality of fluid transport lines for transporting the first fluid, the second fluid and the sample to the mixing assembly;
   a controller coupled to the flow path selection assembly for controlling a flow path selection through the flow path selection assembly; and
   a sample introduction assembly coupled to one of the plurality of fluid transport lines, the sample introduction assembly for introducing the sample into the one of the plurality of fluid transport lines, the flow path selection through the flow path selection assembly having a first flow path configuration and a second flow path configuration, the first flow path configuration coupling the first fluid introduction line to the one of the plurality of fluid transport lines coupled to the sample introduction assembly and coupling the second fluid introduction line to another one of the plurality of fluid transport lines not coupled to the sample introduction assembly, and the second flow path configuration coupling the second fluid introduction line to the one of the plurality of fluid transport lines coupled to the sample introduction assembly and coupling the first fluid introduction line to another one of the plurality of fluid transport lines not coupled to the sample introduction assembly, the flow path selection assembly further comprising a housing and a valve assembly, the valve assembly comprising a plurality of path connection assemblies for coupling with the first fluid introduction line, the second fluid introduction line and the plurality of fluid transport lines.

2. The system as recited in claim 1, wherein at least one of the first pumping device and the second pumping device comprises a peristaltic pump.

3. The system as recited in claim 1, further comprising a sample analyzer coupled with the mixing assembly for analyzing the sample.

4. The system as recited in claim 3, wherein the sample analyzer comprises an Inductively Coupled Plasma Mass Spectrometer (ICP-MS).

5. The system as recited in claim 3, wherein the sample analyzer is coupled with the controller for communicating information regarding the dilution of the sample to the controller.

6. The system as recited in claim 5, wherein the controller is configured to change the flow path selection based upon the information regarding the dilution of the sample received from the sample analyzer.

7. The system as recited in claim 1, wherein the first flow rate is at least approximately inversely proportional to the second flow rate.

8. A system for providing constant flow on-line dilution comprising:
   a first pumping device configured to pump at a first flow rate;
   a first fluid introduction line for carrying a first fluid, the first fluid introduction line coupled to the first pumping device for pumping the first fluid at the first flow rate;
   a second pumping device configured to pump at a second flow rate at least substantially different from the first flow rate;
   a second fluid introduction line for carrying a second fluid, the second fluid introduction line coupled to the second pumping device for pumping the second fluid at the second flow rate;
   a flow path selection assembly coupled to the first fluid introduction line and the second fluid introduction line;
   a mixing assembly for mixing the first fluid, the second fluid, and a sample;
   a first fluid transport line coupled to the flow path selection assembly and the mixing assembly for transporting the first fluid and the sample to the mixing assembly;
   a second fluid transport line coupled to the flow path selection assembly and the mixing assembly for transporting the second fluid to the mixing assembly;
   a controller coupled to the flow path selection assembly for controlling a flow path selection through the flow path selection assembly; and
   a sample introduction assembly coupled to the first fluid transport line for introducing the sample into the first fluid transport line, the flow path selection through the flow path selection assembly having a first flow path configuration and a second flow path configuration, the first flow path configuration coupling the first fluid introduction line to the first fluid transport line and coupling the second fluid introduction line to the second fluid transport line, and the second flow path configuration coupling the second fluid introduction line to the first fluid transport line and coupling the first fluid introduction line to the second fluid transport line.

9. The system as recited in claim 8, wherein at least one of the first pumping device and the second pumping device comprises a peristaltic pump.

10. The system as recited in claim 8, further comprising a sample analyzer coupled with the mixing assembly for analyzing the sample.

11. The system as recited in claim 10, wherein the sample analyzer comprises an Inductively Coupled Plasma Mass Spectrometer (ICP-MS).

12. The system as recited in claim 10, wherein the sample analyzer is coupled with the controller for communicating information regarding the dilution of the sample to the controller.

13. The system as recited in claim 12, wherein the controller is configured to change the flow path selection based upon the information regarding the dilution of the sample received from the sample analyzer.

14. The system as recited in claim 8, wherein the first flow rate is at least approximately inversely proportional to the second flow rate.

15. A method for providing constant flow on-line dilution comprising:
    pumping a first fluid through a first fluid introduction line at a first flow rate;
    pumping a second fluid through a second fluid introduction line at a second flow rate at least substantially different from the first flow rate;
    selectively introducing a sample into one of the first fluid and the second fluid using a flow path selection assembly coupled to the first fluid introduction line and the second fluid introduction line;
    transporting the first fluid, the second fluid, and the sample to a mixing assembly coupled to the flow path selection assembly;
    mixing the first fluid, the second fluid, and the sample using the mixing assembly; and
    controlling a flow path selection through the flow path selection assembly, the flow path selection through the flow path selection assembly having a first flow path configuration for introducing the sample into the first fluid before mixing the first fluid and the second fluid, and a second flow path configuration for introducing the sample into the second fluid before mixing the first fluid and the second fluid.

16. The method as recited in claim 15, wherein pumping a first fluid through a first fluid introduction line at a first flow rate comprises pumping the first fluid through the first fluid introduction line using a peristaltic pump.

17. The method as recited in claim 15, further comprising analyzing the sample using a sample analyzer coupled with the mixing assembly.

18. The method as recited in claim 17, wherein the sample analyzer comprises an Inductively Coupled Plasma Mass Spectrometer (ICP-MS).

19. The method as recited in claim 17, wherein the sample analyzer is coupled with a controller coupled to the flow path selection assembly for controlling a flow path selection through the flow path selection assembly, and the sample analyzer communicates information regarding the dilution of the sample to the controller for changing the flow path selection.

20. The method as recited in claim 15, wherein the first flow rate is at least approximately inversely proportional to the second flow rate.

\* \* \* \* \*